US009138381B2

(12) United States Patent
Kempter et al.

(10) Patent No.: US 9,138,381 B2
(45) Date of Patent: Sep. 22, 2015

(54) PRODUCTION OF INORGANIC-ORGANIC COMPOSITE MATERIALS BY REACTIVE SPRAY-DRYING

(71) Applicant: BASF SE, Ludwigshafen (DE)

(72) Inventors: Andreas Kempter, Neustadt (DE); Max Siebert, Ludwigshafen (DE); Heidrun Debus, Eisenberg (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 14/175,635

(22) Filed: Feb. 7, 2014

(65) Prior Publication Data

US 2014/0228334 A1   Aug. 14, 2014

Related U.S. Application Data

(60) Provisional application No. 61/762,350, filed on Feb. 8, 2013.

(51) Int. Cl.
| *B01D 1/18* | (2006.01) |
| *B01J 2/04* | (2006.01) |
| *A61J 3/02* | (2006.01) |
| *A61K 9/14* | (2006.01) |
| *A61K 31/192* | (2006.01) |
| *A61K 31/415* | (2006.01) |
| *A61K 31/58* | (2006.01) |
| *A61J 3/00* | (2006.01) |

(52) U.S. Cl.
CPC . *A61J 3/02* (2013.01); *A61K 9/143* (2013.01); *A61K 9/145* (2013.01); *A61K 31/192* (2013.01); *A61K 31/415* (2013.01); *A61K 31/58* (2013.01); *A61J 3/005* (2013.01); *B01D 1/18* (2013.01); *B01J 2/04* (2013.01)

(58) Field of Classification Search
None
See application file for complete search history.

(56) References Cited

U.S. PATENT DOCUMENTS

| 6,469,611 | B1 * | 10/2002 | Kluge-Weiss et al. | 338/20 |
| 2004/0052865 | A1 | 3/2004 | Gower et al. | |
| 2004/0248975 | A1 * | 12/2004 | Van Brussel et al. | 514/543 |
| 2009/0004262 | A1 | 1/2009 | Shaw et al. | |
| 2009/0029902 | A1 | 1/2009 | Cunningham et al. | |
| 2009/0104275 | A1 * | 4/2009 | Grinberg | 424/497 |
| 2012/0269888 | A1 | 10/2012 | Jetten et al. | |
| 2013/0236392 | A1 * | 9/2013 | Naterer et al. | 423/648.1 |

FOREIGN PATENT DOCUMENTS

| EP | 1905427 | 4/2008 |
| KR | 10-2011-0100857 | 9/2011 |
| WO | WO-01/05731 | 1/2001 |
| WO | WO-2008/000042 | 1/2008 |
| WO | WO-2009/077147 | 6/2009 |
| WO | WO-2012/027378 | 3/2012 |
| WO | WO2013/163246 | 10/2013 |
| WO | WO-2014/122077 | 8/2014 |

OTHER PUBLICATIONS

Elabbadi, Amal et al., "Complexation/encapsulation of green tea polyphenols in mixed calcium carbonate and phosphate micro-particles", *Journal of Microencapsulation* vol. 28 No. 1, pp. 1-9 (2011).
Fujiwara, Masahiro et al., "Calcium carbonate microcapsules encapsulating biomacromolecules", *Chemical Engineering Journal* vol. 137 pp. 14-22, (2008).
Petrov, Alexander I. et al., Protein-Calcium Carbonate Coprecipitation: A Tool for Protein Encapsulation, *Biotechnol. Prog.* vol. 21, pp. 918-925 (2005).
PCT International Search Report in PCT/EP2014/051921, dated May 19, 2014, 3 pages.
Hino, Tomoaki, et al., Development of a new type nozzle and spray-drier for industrial production of fine powders, *European Journal of Pharmaceutics and Biopharmaceutics*, vol. 19 2000, 79-85.
Zuidam, Nicolaas Jan, et al., Chapter 2: Overview of Microencapsulates for Use in Food Products or Processes and Methods to Make Them, *Encapsulation Technologies for Active Food Ingredients and Food Processing*, Springer, XP009145442, ISBN: 978-1-4419-1007-3 2010, 3-29.

* cited by examiner

*Primary Examiner* — Mary F Theisen
(74) *Attorney, Agent, or Firm* — Servilla Whitney LLC

(57) ABSTRACT

Process for producing composite materials by reactive spray-drying, where a liquid phase A, which comprises inorganic cations, and a liquid phase B, which comprises anions which, with the inorganic cations, form a salt that is insoluble in the mixture of the liquid phases are sprayed together using at least one multi-substance nozzle, and where at least one hydrophobic active ingredient is present in dissolved form in at least one liquid spraying phase, and where the salt formed from the cations of phase A and the anions of phase B has a solubility of less than 0.02 mol/l in the neutral aqueous medium.

21 Claims, 1 Drawing Sheet

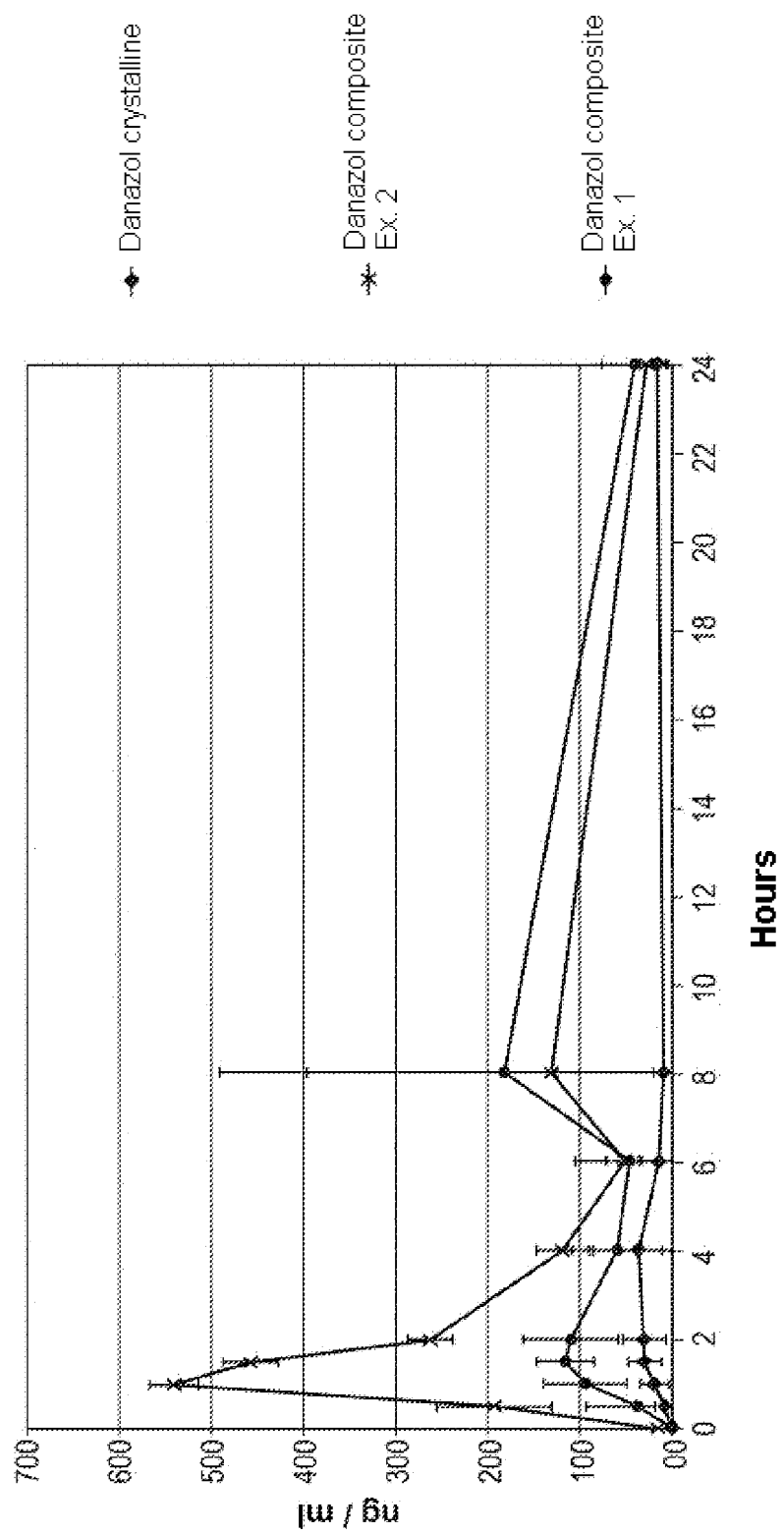

PRODUCTION OF INORGANIC-ORGANIC COMPOSITE MATERIALS BY REACTIVE SPRAY-DRYING

CROSS-REFERENCE TO RELATED APPLICATIONS

This application claims the benefit of priority under 35 U.S.C. §119(e) to U.S. Provisional Application No. 61/762,350, filed Feb. 8, 2013, the entire content of which is incorporated herein by reference in its entirety.

TECHNICAL FIELD

The present invention relates to a process for producing inorganic-organic composite materials by reactive spray-drying, where the organic phase in the composite materials constitutes at least one organic active ingredient and the inorganic phase constitutes an inorganic salt that is sparingly soluble under standard conditions. Furthermore, the invention relates to corresponding composite materials and to the use thereof.

BACKGROUND

Inorganic-organic materials based on calcium carbonate in which biomolecules can be embedded are known per se, where the materials are obtained by precipitation processes, and where the active ingredients embedded in the calcium carbonate matrix are water-soluble substances. For example, A. Elabbadi et al., Journal of Microencapsulation, 2011; 28(1):1-9, describe the microencapsulation of green tea extracts into microparticles of calcium carbonate and phosphates. M. Fujiwara et al, Chemical Engineering Journal 137 (2008) 14-22, describe the encapsulation of water-soluble biomolecules such as bovine serum albumin into calcium carbonate microcapsules. A. I. Petrov et al., Biotechnol. Prog. 2005, 21, 918-925 also describe the embedding or adsorption of water-soluble biomolecules such as, for example, bovine serum albumin into calcium carbonate by coprecipitation.

US 2009/0104275 describes the production of microencapsulated insulin, where the microencapsulation can take place by coprecipitation.

US 2009029902 describes complexes of calcium carbonate and proteins with calcium carbonate binding domains. The complexes can be obtained by precipitation from aqueous slurries.

WO 2008000042 describes nanoparticulate formulations of sparingly water-soluble active ingredients, where the formulations are obtained by grinding the active ingredients with water-soluble inorganic salts.

In WO 0105731, amorphous glass-like products obtained by melting inorganic salt mixtures are mechanically mixed with active ingredients and granulated.

WO 2009077147 describes pharmaceutical formulations which are obtained by mixing an active ingredient with a particulate basic solid, where the basic particulate solid is an alkali metal or alkaline earth metal salt.

EP-A 1905427 describes the embedding of active ingredients into an inorganic matrix, where only readily water-soluble inorganic salts such as, for example, sodium carbonate are described as inorganic matrix.

WO 2012/027378 describes the production of particulate active ingredient preparations, where an inorganic carrier substance such as, for example, calcium carbonate and a hydrophobic pharmaceutical active ingredient are precipitated together in a mixing chamber.

However, it is a disadvantage of the precipitation processes in a mixing chamber that the mixing chambers tend to rapidly block. Furthermore, the coprecipitates have a tendency toward recrystallization of the active ingredient, which results in poorer release of the active ingredient and therefore deterioration in bioavailability.

One aspect of the present invention provides a simple and economically feasible process for producing inorganic-organic composite materials comprising biologically active ingredients which avoids the disadvantages of the prior art.

SUMMARY

Therefore, the present invention relates to a process for producing composite materials by reactive spray-drying, where a liquid phase A, which comprises inorganic cations, and a liquid phase B, which comprises anions which, with the inorganic cations, form a salt that is insoluble in the mixture of the liquid phases are sprayed together using at least one multi-substance nozzle, and where at least one hydrophobic active ingredient is present in dissolved form in at least one liquid spraying phase, and where the salt formed from the cations of phase A and the anions of phase B has a solubility of less than 0.02 mol/l in the neutral aqueous medium.

In one or more embodiments, the inorganic cations of phase A are selected from the group consisting of magnesium ions, calcium ions and zinc ions. In a preferred embodiment, the inorganic cations of phase A used are calcium ions.

In one or more embodiments, the liquid phase A is a solution of salts of the inorganic cations and the salts are selected from the group consisting of calcium chloride, calcium nitrate, calcium acetate, magnesium chloride, magnesium nitrate, magnesium acetate, magnesium citrate, magnesium lactate, zinc chloride, zinc nitrate and zinc acetate.

In one or more embodiments, the liquid phase B used is a solution of salts selected from the group consisting of ammonium, alkali metal or magnesium salts of carbonates, hydrogencarbonates, sulfates, phosphates and hydrogenphosphates.

In yet another embodiment, the liquid phase B used is a solution of salts selected from the group consisting of ammonium, alkali metal or magnesium salts of citric acid, lactic acid and oxalic acid.

In one or more embodiments, the salt formed from the cations of phase A and the anions of phase B that is used is a calcium salt selected from the group consisting of carbonates, phosphates, sulfates, hydroxylapatites, citrates, lactates and oxalates.

In one or more embodiments, the liquid phases are solutions and the solvents present are water or organic solvents or mixtures thereof. In one or more preferred embodiments, the organic solvent used is ethanol.

In one or more embodiments, the hydrophobic active ingredient is used in the form of an ethanolic or aqueous-ethanolic solution.

In one or more embodiments, a surfactant may be added to the liquid phase which comprises the hydrophobic active ingredient. In one or more embodiments, the surfactant is added in amounts of from 2 to 50% by weight, based on the amount of active ingredient, to the liquid phase which comprises the hydrophobic active ingredient. The surfactant may be selected from the group consisting of polyoxyalkylated fatty acid esters and polyoxyalkylated fatty alcohol ethers.

In one or more embodiments, the multi-substance nozzle used is an ultrasonic nozzle. An atomization gas is used during the spray-drying. In one or more embodiments, spraying drops with a median diameter of 10 to 200 μm μm are produced.

In one or more embodiments, the hydrophobic active ingredient is present in phase A. In yet another embodiment, the hydrophobic active ingredient is present in phase B. In one embodiment, phase A comprises a calcium salt and phase B comprises ammonium carbonate or sodium carbonate. In another embodiment, phase A comprises a calcium salt and phase B comprises ammonium acetate or sodium acetate.

Further, the present invention relates to a composite material comprising at least one amorphous hydrophobic active ingredient in an amorphous salt matrix with a solubility in the neutral aqueous medium of less than 0.02 mol/l, obtained by a spraying process according to one or more embodiments of the present invention. In one or more preferred embodiments, the composite material comprises at least one amorphous hydrophobic active ingredient in an amorphous salt matrix of at least one salt selected from the group of calcium, magnesium and zinc salts. In yet another preferred embodiment, the at least one amorphous hydrophobic active ingredient in an amorphous salt matrix is calcium carbonate.

In one or more embodiments, the composite material further comprises a surfactant. In one or more embodiments, the surfactant may be selected from the group consisting of polyoxyethylenated esters of castor oil or hydrogenated castor oil. In yet another embodiment, the surfactant is sodium laurylsulfate.

BRIEF DESCRIPTION OF THE DRAWINGS

FIG. 1 shows the plasma level of the composite materials according to Examples 1, 2 and Comparative Example I.

DETAILED DESCRIPTION

A process has been found for producing composite materials by reactive spray-drying, where a liquid phase A, which comprises inorganic cations, and a liquid phase B, which comprises anions which, with the inorganic cations, form a salt that is insoluble in the mixture of the liquid phases, are sprayed together using a multi-substance nozzle, and where at least one hydrophobic active ingredient is present in dissolved form in at least one liquid phase, and the salt formed from the cations of phase A and the anions of phase B has a solubility of less than 0.02 mol/l in the neutral aqueous medium. Neutral aqueous medium means a pH of 7+/−0.5. In one or more embodiments, aqueous medium means a purely aqueous medium without the presence of further solvents. The solubility refers to the solubility under standard conditions at 20° C. and 0.101325 MPa.

The hydrophobic active ingredient can be present in dissolved form in one of the liquid phases A or B or be introduced into the process in dissolved form in a further liquid phase.

Within the context of the present invention, composite materials are those materials in which one component is embedded into a matrix of another component. In the composite materials obtained by the process according to the invention, a hydrophobic organic active ingredient is present in embedded form in a matrix of a salt of inorganic cations (the "salt matrix"), with the salt matrix being present in amorphous form. In one preferred embodiment, the hydrophobic active ingredient is also in the amorphous state. Amorphous state in this connection means that not more than 5% by weight of the active ingredient or of the salt matrix are present in crystalline form, this state being determined by means of XRD (X-ray diffraction).

A suitable salt matrix according to the invention is salts which can be obtained under certain conditions by bringing at least two liquid phases into contact, of which one phase comprises inorganic cations and a second or further phase comprises anions which form sparingly water-soluble salts with the cations of the other liquid phase. As defined, the resulting salts are only sparingly soluble in water, but readily soluble in an acidic medium, sometimes with decomposition.

According to the invention, inorganic cations of the salt matrix are metallic cations which are preferably physiologically well tolerated. In particular, suitable cations are calcium ions, magnesium ions or zinc ions or mixtures thereof. Particular preference is given to calcium ions.

Suitable counterions of the salt matrix are both inorganic and organic anions, the intention being for the resulting salts as described to be insoluble in the neutral aqueous medium. Which anions are suitable is also governed by the type of cation. Thus, for example, some calcium salts are sparingly soluble in water whereas the corresponding magnesium salts are readily soluble in water. For all of the anions specified below, the solubility of the possible salts should thus be ascertained. This is possible for the person skilled in the art in a simple manner since these are known in the literature.

Suitable inorganic anions of the resulting sparingly water-soluble salt matrix are selected from the group consisting of carbonate, phosphate, sulfate or mixed anions such as, for example, hydroxylapatite.

According to one embodiment, suitable organic anions of the sparingly water-soluble salt matrix are anions of physiologically compatible organic mono- or polybasic acids. This embodiment refers to a salt matrix which comprises calcium salts as salts that are sparingly soluble in water. Suitable calcium salts are selected from the group consisting of calcium citrate, calcium lactate and calcium oxalate.

The liquid phase A which comprises the cations of the sparingly water-soluble salt matrix to be formed is obtained by dissolving corresponding salts that are readily soluble in the selected medium. Suitable salts are calcium chloride, calcium nitrate, calcium acetate, magnesium chloride, magnesium nitrate, magnesium acetate, magnesium citrate, magnesium lactate, zinc chloride, zinc nitrate or zinc acetate. The salts can, if applicable, also be used in the form of their mono-, di- or semihydrates.

The salts with which the cations of the sparingly water-soluble salt matrix to be formed in the liquid phase A are introduced as solution into the process are those which are preferably readily water-soluble or are readily soluble in organic solvents or organic-aqueous mixtures.

The salts with which the anions of the sparingly water-soluble salt matrix to be formed in the liquid phase A are introduced as solution into the process are ammonium salts or alkali metal salts that are readily water-soluble or readily soluble in a hydrophilic organic solvent or readily soluble in aqueous-organic mixtures. Furthermore, also of suitability are correspondingly readily soluble magnesium salts. Suitable salts are in particular readily water-soluble carbonates, hydrogencarbonates, sulfates, phosphates, hydrogenphosphates. Furthermore, organic salts such as ammonium, alkali metal or magnesium salts of citric acid, lactic acid or oxalic acid are suitable. In one preferred embodiment, the liquid phase B via which the anion component of the sparingly water-soluble salt matrix is introduced is purely aqueous. Optionally, phase B can also comprise organic solvents.

How the salt components of the liquid phases A and B are combined depends on the type of desired sparingly water-soluble salt matrix. It is obvious that a cation which is introduced in liquid phase A as cation-supplying component for the sparingly water-soluble salt matrix cannot simultaneously serve as cation of an anion-supplying component dissolved in liquid phase B.

The cations of liquid phase A must in any case be able to form with the anions of liquid phase B a sparingly water-soluble salt with a solubility of less than 0.02 mol/l (at 20° C. and 0.1 MPa).

Thus, for example, a magnesium salt such as magnesium chloride can be reacted as cation-supplying salt of phase A with an ammonium carbonate or alkali metal carbonate salt dissolved in phase B to give a corresponding sparingly soluble magnesium carbonate. Similarly, for example, a calcium salt such as calcium chloride can be reacted as cation-supplying salt of phase A with a magnesium salt such as magnesium citrate dissolved in phase B to give a corresponding sparingly soluble calcium citrate.

Suitable solvents for the different liquid phases to be sprayed are, besides water, also hydrophilic organic solvents which have unlimited miscibility with water, such as methanol, ethanol, glycerol, 1,2-propylene glycol, low molecular weight polyethylene glycols such as PEG 200, PEG 300, PEG 600 or acetone, acetonitrile, dimethyl sulfoxide, dimethylformamide, N-methylpyrrolidone, 2-methoxyethanol or tetrahydrofuran. In one preferred embodiment, the hydrophilic organic solvent used is ethanol.

The respective concentration of the feed materials in the solvent is case-specific and arises from the particular solubilities of the components used. However, in the liquid phases, preference is given to concentrations of 0.1 to 10 mol/l for the salt components to be used. In one preferred embodiment, a concentration of 0.5 to 2 mol/l for the salt components is used. The concentration of the hydrophobic active ingredients in the liquid phase can be 1 to 100 g/l. In one preferred embodiment, the concentration of the hydrophobic active ingredients in the liquid phase can be 10 to 40 g/l.

The salt matrix as target substance of the reactive spray-drying is no longer soluble in the mixture of the solvents of the fluid phases and is also sparingly soluble in water (less than 0.02 mol/l).

According to one embodiment, the hydrophobic active ingredient component is introduced into the process via an organic solution, and the mixture of all liquid phases constitutes an aqueous-organic solvent mixture.

For all of the embodiments specified below, when using an organic solvent, preference is given to using ethanol.

According to one embodiment, phase A comprises a mixture of water and an organic solvent and also the hydrophobic active ingredient, and phase B is a purely aqueous phase which comprises no further solvent. According to a further embodiment, phases A and B are purely aqueous phases and the hydrophobic active ingredient is introduced into the spraying process in a further liquid phase, dissolved in an organic solvent. According to another embodiment, the phase is a purely aqueous phase and phase B is an aqueous-organic phase which also comprises the hydrophobic active ingredient.

According to a further embodiment, different hydrophobic active ingredients can also be introduced into the process. These can be dissolved together in one phase or introduced via different phases.

According to a further preferred embodiment of the invention, at least one surfactant is added to one of the liquid phases A or B or optionally to a further liquid phase. According to one embodiment of the invention, the hydrophobic active ingredient component is accordingly introduced into the spraying process via an aqueous or aqueous-organic phase which additionally comprises at least one surfactant. According to a further embodiment of the invention, the hydrophobic active ingredient component is present together with the surfactant in phase A. According to one embodiment of the invention, the hydrophobic active ingredient component is present together with the surfactant in phase B. According to a further embodiment of the invention, the hydrophobic active ingredient component is present together with the surfactant in an additional liquid phase. According to a particularly preferred embodiment, the liquid phase comprising surfactant and hydrophobic active ingredient is a purely aqueous phase.

Suitable surfactants are selected from the group of anionic, cationic, nonionic and amphiphilic surfactants.

Suitable anionic surfactants are inter alia, sodium, potassium, magnesium and calcium salts of fatty acids and food fatty acids. Suitable anionic surfactants are for example sodium lauryl sulfate, ammonium lauryl sulfate, sodium cetylstearyl sulfate, docusate sodium, docusate potassium or docusate calcium.

A suitable cationic surfactant is for example cetylpyridinium chloride.

In principle, suitable surfactants are mono- and diglycerides of fatty acids and food fatty acids, acetic acid esters, lactic acid esters such as sodium or calcium stearoyl 2-lactate, citric acid esters such as, for example, triethyl citrate, tartaric acid esters, for example, stearyl tartrate, diacetyltartaric acid esters, mixed acetic and tartaric acid esters, sugar esters of fatty acids and food fatty acids, sugar glycerides, propylene glycol esters of food fatty acids, polyglycerol polyricinoleate or propylene glycol esters of food fatty acids.

Suitable nonionic surfactants are for example fatty alcohols and sterols such as cetyl alcohol, stearyl alcohol, cetylstearyl alcohol or cholesterol.

Suitable nonionic surfactants are for example sorbitan esters, which may also be polyoxyalkylated, for example sorbitan monostearate, sorbitan stearate, sorbitan monolaurate, sorbitan monooleate, sorbitan monopalmitate, polysorbate 20 (polyoxyethylene-(20) sorbitan monolaurate), polysorbate 21 (polyoxyethylene-(4) sorbitan monolaurate), polysorbate 40 (polyoxyethylene-(20) sorbitan monopalmitate), polysorbate 60 (polyoxyethylene-(20) sorbitan monostearate), polysorbate 61 (polyoxyethylene-(4) sorbitan monostearate), polysorbate 65 (polyoxyethylene-(20) sorbitan tristearate), polysorbate 80 (polyoxyethylene-(20) sorbitan monooleate), polysorbate 81 (polyoxyethylene-(5) sorbitan monooleate), polysorbate 85 (polyoxyethylene-(20) sorbitan trioleate) or polysorbate 120 (polyoxyethylene-(20) sorbitan monoisostearate).

Suitable nonionic surfactants are also sucrose fatty acid esters such as, for example, sucrose stearate, sucrose laurate, sucrose palmitate, sucrose oleate, sucrose caprylate, sucrose decanoate, sucrose myristate, sucrose pelargonate, sucrose undecanoate, sucrose tridecanoate, sucrose pentadecanoate or sucrose heptadecanoate.

Also suitable are polyoxyethylene fatty acid glycerides such as Macrogol-1500 glycerol triricinoleate, Macrogol glycerol hydroxystearate Ph.Eur. (Kolliphor™ RH40), Macrogol glycerol ricinoleate Ph.eur. (Kolliphor™ EL), Macrogol-1000 glycerol monolaurate, Macrogol-1000 glycerol monostearate, Macrogol-1000 glycerol monooleate.

Also suitable are polyoxyethylene fatty acid esters such as Macrogol-15 hydroxystearate (Kolliphor™ HS15), Macrogol stearate 400 (Ph.Eur.), polyoxyl-40 stearate or polyoxyl-50 stearate.

Also suitable are polyoxyethylene fatty alcohol ethers such as Macrogol lauryl ether, polyoxyethylene-23 lauryl ether or polyoxyl-10 oleyl ether.

Likewise suitable are glycerol fatty acid esters such as glycerol monostearate.

Suitable amphiphilic surfactants are for example poloxamers such as poloxamer 188, poloxamer 237, poloxamer 338 or poloxamer 407. In one preferred embodiment, the amphiphilic surfactant is poloxamer 188. Also suitable as amphiphilic surfactants are solubilizing polymers such as Soluplus, a copolymer of PEG 6000, N-vinylcaprolactam and vinyl acetate and in the weight ratio 13/57/30. A suitable amphiphilic surfactant is also lecithin.

According to one embodiment of the invention, sodium lauryl sulfate is a preferred surfactant.

According to a further preferred embodiment, the surfactants used are polyoxyethylenated castor oils and hydrogenated castor oils such as Macrogol glycerol hydroxystearate Ph.Eur. or Macrogol glycerol ricinoleate Ph. Eur.

According to a further preferred embodiment, the surfactant used is tocopherol polyethylene glycol succinate with PEG 1000, 1500 or 2000.

The surfactants can be added in amounts of from 2 to 50% by weight based on the amount of active ingredient. In one preferred embodiment, the surfactants can be added in amounts of from 5 to 45% by weight, based on the amount of active ingredient.

Hydrophobic organic active ingredients can be pharmaceutical or cosmetic active ingredients, crop protection agents, nutritional supplements or pigments. Hydrophobic active ingredients have a solubility in water of less than 0.1 g/l at 20° C. and a pressure of 0.101325 MPa.

Pharmaceutical hydrophobic active ingredients can be for example: benzodiazepines, antihypertensives, vitamins, cytostatics—in particular taxol, anesthetics, neuroleptics, antidepressants, antivirals, such as, for example, anti-HIV drugs, antibiotics, antimycotics, antidementia agents, fungicides, chemotherapeutics, urologics, thrombocyte aggregation inhibitors, tyrosine kinase inhibitors, sulfonamides, spasmolytics, hormones, immunoglobulins, sera, thyroid therapeutics, psychopharmaceuticals, Parkinson's drugs and other antihyperkinetics, ophthalmics, neuropathy preparations, calcium metabolism regulators, muscle relaxants, narcotics, lipid-lowering drugs, liver therapeutics, coronary drugs, cardiac drugs, immunotherapeutics, regulatory peptides and their inhibitors, hypnotics, sedatives, gynecological drugs, gout remedies, fibrinolytics, enzyme preparations and transport proteins, enzyme inhibitors, emetics, blood-flow stimulators, diuretics, diagnostics, corticoids, cholinergics, biliary therapeutics, antiasthmatics, broncholytics, beta-receptor blockers, calcium antagonists, ACE inhibitors, arteriosclerosis drugs, antiphlogistics, anticoagulants, antihypertensives, antihypoglycemics, antihypertonics, antifibrinolytics, antiepileptics, antiemetics, antidotes, antidiabetics, antiarrhythmics, antianemics, antiallergics, anthelmintics, analgesics, analeptics, aldosterone antagonists, slimming aids.

To produce the spray solutions, the individual components are dissolved in the solvents suitable in each case. The different liquid phases are supplied to the spraying nozzles separately.

All conventional spraying devices are suitable for carrying out the process according to the invention.

Suitable spraying nozzles are multi-substance nozzles such as two-substance nozzles, three-substance nozzles or four-substance nozzles. Such nozzles can also be configured as so-called "ultrasonic nozzles". Such nozzles are commercially available per se.

Furthermore, depending on the type of nozzle, an atomization gas can also be supplied. The atomization gas used can be air or an inert gas such as nitrogen or argon. The gas pressure of the atomization gas can be up to 1 MPa absolute. In one preferred embodiment, the gas pressure of the atomization gas is within the range of 0.12 to 0.5 MPa absolute.

According to one embodiment, special nozzles in which the different liquid phases are mixed within the nozzle body and then atomized are also suitable.

One embodiment of the invention relates, as mentioned, to ultrasonic nozzles. Ultrasonic nozzles can be operated with or without atomization gas. In ultrasonic nozzles, the atomization takes place in that the phase to be atomized is set vibrating. Depending on the nozzle size and design, the ultrasonic nozzles can be operated with a frequency of 16 to 120 kHz.

The throughput of liquid phase to be sprayed per nozzle is governed by the nozzle size. The throughput can be 500 g/h to 1000 kg/h. When producing commercial amounts, the throughput is preferably in the range from 10 to 1000 kg/h.

If no atomization gas is used, then the liquid pressure can be 0.2 to 20 MPa absolute. If an atomization gas is used, then the liquid can be supplied without pressure.

Furthermore, a drying gas such as air or one of the mentioned inert gases is supplied to the spray-drying device. The drying gas can be supplied cocurrently or countercurrently to the sprayed liquid. In one preferred embodiment, the drying gas is supplied cocurrently to the sprayed liquid. The entry temperature of the drying gas can be 120 to 220° C. the exit temperature 50 to 90° C. In one preferred embodiment, the entry temperature of the drying gas can be 150 to 200° C., and the exit temperature can be 50 to 90° C.

As already mentioned, the orders of magnitude of the spraying parameters to be used such as throughput, gas pressure or nozzle diameter are decisively governed by the size of the devices. The devices are commercially available and corresponding orders of magnitude are usually recommended by the manufacturer.

According to one or more preferred embodiments of the invention, the spraying process is operated such that the average drop size of the sprayed phases is 10 to 200 μm. The average drop size can be determined by means of laser diffraction or high-speed camera coupled with image evaluation.

The statements above relating to the spraying process can be applied to all of the preferred and particularly preferred embodiments described below. Preferred spraying parameters are also preferred in connection with the embodiments below.

According to a preferred embodiment, the invention relates to a process for producing composite materials by reactive spray-drying, where a liquid phase A which comprises inorganic cations and constitutes a solution of salts of the inorganic cations, where the salts are selected from the group consisting of calcium chloride, calcium nitrate, calcium acetate, magnesium chloride, magnesium nitrate, magnesium acetate, magnesium citrate, magnesium lactate, zinc chloride, zinc nitrate and zinc acetate, and a liquid phase B which comprises anions which form with the inorganic cations a salt that is insoluble in the mixture of the liquid phases and constitutes a solution of salts selected from the group consisting of ammonium, alkali metal or magnesium salts of acetates, carbonates, hydrogencarbonates, sulfates, phosphates, hydrogenphosphates and hydroxides, are sprayed together using at least one multi-substance nozzle, and where at least one hydrophobic active ingredient is present in at least one liquid spraying phase, in dissolved form, and where the salt formed from the cations of phase A and the anions of phase B has a solubility of less than 0.02 mol/l in the neutral aqueous medium. According to one or more preferred embodiments of the invention, the solvents of the liquid phases used are water or ethanol or water/ethanol mixtures.

According to a further preferred embodiment, the invention relates to a process for producing composite materials by reactive spray-drying, where a liquid phase A which comprises inorganic cations and constitutes a solution of salts of the inorganic cations and the salts are selected from the group of calcium chloride, calcium nitrate, calcium acetate, magnesium chloride, magnesium nitrate, magnesium acetate, magnesium citrate, magnesium lactate, zinc chloride, zinc nitrate and zinc acetate, and a liquid phase B which comprises anions which form with the inorganic cations a salt that is insoluble in the mixture of the liquid phases and constitutes a solution of salts selected from the group consisting of ammonium, akali metal or magnesium salts of acetates, carbonates, hydrogencarbonates, sulfates, phosphates, hydrogenphosphates and hydroxides, are sprayed together using at least one multi-substance nozzle, and where at least one hydrophobic active ingredient is present in dissolved form together with a surfactant in at least one liquid spraying phase, and where the salt formed from the cations of phase A and the anions of phase B has a solubility of less than 0.02 mol/l in the neutral aqueous medium. According to one or more preferred embodiments of the invention, the solvents of the liquid phases used are water or ethanol or water/ethanol mixtures. According to one or more preferred embodiments of the invention, the surfactants used are nonionic surfactants.

According to a particularly preferred embodiment, the invention relates to a process for producing composite materials by reactive spray-drying, where a liquid phase A which comprises inorganic cations is used and where the liquid phase A constitutes a solution of salts of the inorganic cations, and the salts are selected from the group consisting of calcium chloride and calcium acetate, and a liquid phase B which comprises anions which, with the inorganic cations, form a salt that is insoluble in the mixture of the liquid phases, and where the liquid phase B used is a solution of salts selected from the group consisting of ammonium or alkali metal salts of acetates, carbonates, hydrogencarbonates, sulfates, phosphates, hydrogenphosphates and hydroxides, and where the liquid phases A and B and optionally further liquid phases are sprayed together using at least one multi-substance nozzle, and where at least one hydrophobic active ingredient is present in dissolved form in at least one liquid spraying phase, and where the salt formed from the cations of phase A and the anions of phase B has a solubility of less than 0.02 mol/l in the neutral aqueous medium. According to one or more preferred embodiments of the invention, the solvents of the liquid phases used may be water, ethanol or water/ethanol mixtures. According to one or more preferred embodiments of the invention, the active ingredient is dissolved in ethanol, optionally in the presence of a surfactant, which is preferably a nonionic surfactant, and can be added to phase A or to phase B. According to one or more preferred embodiments of the invention, the ammonium or alkali metal salts of phase B are acetates or carbonates.

If, according to one of the preferred or particularly preferred embodiments described above, a nonionic surfactant is used in the liquid phase which comprises the hydrophobic active ingredient, then preference is given to using a polyoxyalkylated fatty acid ester, in particular Macrogol hydroxystearate, Macrogol glycerol hydroxystearate or Macrogol glycerol ricinoleate.

The resulting composite materials constitute an amorphous sparingly water-soluble salt matrix in which at least one active ingredient present in amorphous form is embedded. Furthermore, the composite material comprises water-soluble salt components.

The composite materials according to the invention which are produced using the reactive spraying technology have particular advantages over known technologies. Surprisingly, the reaction time can be considerably reduced by the reactive spray-drying compared to precipitation. The spraying process produces a powder which can be further processed without complicated work-up (filtration, downstream drying).

Compared with the described processes, the reactive spray-drying has the advantage that it is based on a technology which is scalable and is easy to realize under GMP conditions. The composites are particularly suitable for the formulation of sparingly soluble active ingredients which have a high melting point (>180° C.) and an inadequate thermal stability (decomposition at high temperatures, decomposition in the melt) and are therefore less suitable for conventional processes such as melt extrusion.

The composites exhibit a significantly more rapid and more complete active ingredient release in synthetic gastric juice compared to the crystalline substance.

Being spray-dried powders, the composite materials are suitable for processing in solid administration forms.

For example, they are suitable for producing adhesive granules by wet granulation (mixer or fluidized bed) by adding binders such as carboxymethylcellulose Na, hydroxypropylmethylcellulose, homo- and copolymers of N-vinylpyrrolidone such as PVP or copolymers of N-vinylpyrrolidone and vinyl acetate, starches or gelatin.

They are also suitable for producing dry granules with or without the addition of dry binders such as e.g. Kollidon® VA 64 Fine, for example using a roller compactor.

Furthermore, the powders or granules can be mixed with other auxiliaries or active ingredients and be packaged in sachets for taking as redispersible powders.

Furthermore, the powders or granules can be packaged into hard capsules.

Furthermore, the powders or granules can be compressed to give tablets, for example with addition of flow regulators (Aerosil 200=highly disperse SiO2), lubricants such as Mg stearate, Ca stearate, stearic acid, sodium stearyl fumarate, PEG with average molecular weights $M_W$ of 1000-8000, disintegrants such as crospovidone or sodium starch glycolate). Furthermore, wetting agents such as poloxamer 188 or sodium lauryl sulfate can also be added to the tableting mixture.

The composite materials according to the invention are also suitable for producing effervescent tablets. Here, an effervescent mixture which consists of sodium bicarbonate and an acid (citric acid or tartaric acid) is usually added to the tableting mixture. In the case of the composite materials according to the invention, it is possible, depending on the composition, to dispense with the addition of sodium bicarbonate, for example if the matrix consists of calcium carbonate. In this case, the amount of acid is adapted to the amount of calcium carbonate.

EXAMPLES

Analytical Methods

The active ingredient release was determined in accordance with the USP, chapter <711>, Dissolution, paddle apparatus at 100 rpm. The amount of sample was standardized to 100 mg of active ingredient.

Release medium A: 0.08 m HCl, pH 1.1

Release medium B: as release medium A, but additionally 0.1% by weight polysorbate 80 were added to the release medium.

The determination is carried out at 20+/−5° C. and atmospheric pressure (0.101325 MPa).

The amorphous state was determined by means of XRD.

Measuring instrument: diffractometer D 8 Advance with 9-fold sample changer (Bruker/AXS)

Measurement type: θ-θ geometry in reflection
Angle range 2 theta: 2-80°
Interval: 0.02°
Measuring time per angle interval: 4.8 s
Divergence slit: Göbel mirror with 0.4 mm orifice plate
Antiscattering slit: Soller slit
Detector: Sol-X detector
Temperature: room temperature Example 1

Danazol-Calcium Carbonate Composite
Phase A: $CaCl_2$, danazol
0.5 mol/l $CaCl_2$ dissolved in ethanol, concentration of danazol in the solution: 10 g/l
Phase B: solution of 0.5 mol/l $Na_2CO_3$ in deionized water The spraying device was a device from Büchi, B290, equipped with a three-substance nozzle of the type 0465555

Spraying Parameters:
Spraying device: Büchi B290; nozzle: outer channel 2.0 mm diameter, inner channel 0.7 mm diameter, gas channel 2.8 mm diameter
Atomization gas: nitrogen, 819 l/h
Pump throughput of spraying liquid: 15 ml/min
Drying gas: nitrogen, throughput: 65 m$^3$/h
Tower entry temperature: 180° C.
Tower exit temperature: 62-65° C.

Release test: after 120 min in release medium B, 10% by weight of the danazol were released.

According to determination with XRD, the composites were amorphous.

Example 2

Danazol-Calcium Carbonate Composite with Surfactant
Phase A: calcium acetate 0.25 mol/l in deionized water
Phase B: ammonium acetate 0.25 mol/l, danazol 5 g/l, Kolliphor™ RH40 5% by weight, based on active ingredient A corresponding amount of ammonium carbonate was dissolved in 150 g of deionized water and admixed with 300 g of the ethanolic active ingredient solution. The resulting mixture was stirred at 40° C. until a clear solution was formed.

The nozzle used was a 120 kHz ultrasonic spray-dryer nozzle type 06-04-00445, equipped with a micropore capillary for two-fold liquid introduction type 06-05-00290.

Spraying Parameters:
Spraying device: Büchi B290; ultrasound nozzle: two-substance nozzle, Sonotek, power 5 W cooling ultrasonic nozzle with 60%, gas passage, cooling gas nitrogen, nozzle temperature 63° C.
Pump throughput of spraying liquid: 4 ml/min
Drying gas: nitrogen, throughput: 65 m$^3$/h, tower entry temperature: 130° C.,
Tower exit temperature: 68° C.

Release test: after 120 min in release medium A, 35% by weight of the danazol were released.

According to XRD, the composites were amorphous.

Example 3

Danazol-Calcium Carbonate Composite with Surfactant
A composite with Kolliphor™ EL as surfactant was obtained analogously to Example 2.

Release test: after 120 min in release medium A, 35% by weight of the danazol were released.

According to XRD, the composites were amorphous.

Example 4

Estradiol-Calcium Carbonate Composite
Phase A: solution of 0.5 mol/l calcium chloride and 10 g/l estradiol in ethanol.
Phase B: solution of 0.5 mol/l $CaCO_3$ in deionized water The spraying device used was a device from Büchi, B290, equipped with a three-substance nozzle of the type 0465555.

Spraying Parameters:
Spraying device: Büchi B290; nozzle: outer channel 2.0 mm diameter, inner channel 0.7 mm diameter, gas channel 2.8 mm diameter
Atomization gas: nitrogen, 819 l/h
Pump throughput of spraying liquid: 15 ml/min
Drying gas: nitrogen, throughput: 65 m$^3$/h
Tower entry temperature: 170° C.
Tower exit temperature: 48-52° C.

Release test: after 120 min in release medium B, 30% by weight of the estradiol were released.

According to determination with XRD, the composites were amorphous.

Example 5

Itraconazole-Calcium Carbonate Composite
Phase A: calcium acetate
0.25 mol/l calcium acetate dissolved in ethanol. 5 g/l itraconazole dissolved in THF, then both solutions were mixed. Ethanol/THF solvent mixture after mixing: 60/40 (ethanol/THF) 60/40
Phase B: solution of 0.25 mol/l $(NH_4)_2CO_3$ in deionized water.

The spraying device used was a device from Büchi, B290, equipped with a three-substance nozzle of the type 0465555

Spraying Parameters:
Spraying device: Büchi B290; nozzle: outer channel 2.0 mm diameter, inner channel 0.7 mm diameter, gas channel 2.8 mm diameter
Atomization gas: nitrogen, 819 l/h
Pump throughput of spraying liquid: 15 ml/min
Drying gas: nitrogen, throughput: 65 m$^3$/h
Tower entry temperature: 210° C.
Tower exit temperature: 68-72° C.

Release test: after 120 min in release medium A, 30% by weight of the itraconazole were released.

According to determination with XRD, the composites were amorphous.

Example 6

Naproxen-Calcium Carbonate Composite
Phase A: calcium acetate
0.25 mol/l calcium acetate dissolved in deionized water.
Phase B: solution of 0.25 mol/l $(NH_4)_2CO_3$ in deionized water/acetone (60/40) and 10 g/l naproxen The spraying device was a device from Büchi, B290, equipped with a three-substance nozzle of the type 0465555.

Spraying Parameters:

Spraying device: Büchi B290; nozzle: outer channel 2.0 mm diameter, inner channel 0.7 mm diameter, gas channel 2.8 mm diameter Atomization gas: nitrogen, 819 l/h Pump throughput of spraying liquid: 12 ml/min Drying gas: nitrogen, throughput: 65 m$^3$/h Tower entry temperature: 220° C.

Tower exit temperature: 68-70° C.

Release test: after 120 min in release medium A, 45% by weight of the naproxen were released.

According to determination with XRD, the composites were amorphous.

Example 7

Celecoxib-Calcium Carbonate Composite

Phase A: calcium acetate 0.25 mol/l in deionized water

Phase B: ammonium acetate 0.25 mol/l, celecoxib 5 g/l, 5% by weight Kolliphor™ RH40, based on active ingredient, in a mixture of deionized water and EtOH 1:2 (weight ratio).

A corresponding amount of ammonium carbonate was dissolved in 150 g of deionized water and admixed with 300 g of the ethanolic active ingredient solution. The resulting mixture was stirred at 40° C. until a clear solution was formed.

The nozzle used was a 120 kHz ultrasonic spray-dryer nozzle type 06-04-00445, SonoTek, USA, equipped with a micropore capillary for two-fold liquid introduction type 06-05-00290.

Spraying Parameters:

Spraying device: Büchi B290; ultrasonic nozzle: two-substance nozzle, Sonotek, power 5 W cooling ultrasonic nozzle with 60% gas passage, cooling gas nitrogen, nozzle temperature 52° C.

Pump throughput of spraying liquid: 4 ml/min

Drying gas: nitrogen, throughput: 65 m$^3$/h, tower entry temperature: 132° C., tower exit temperature: 68-70° C.

Release test: after 120 min in release medium A, 20% by weight of the celecoxib were released.

According to XRD, the composites were amorphous.

Comparative Example I

Spraying of Pure Danazol

As spraying solution, a solution obtained analogously to Example 2, phase B was sprayed under the spraying conditions given in Example 2.

Release test: after 120 min in release medium A comprising 0.1% by weight polysorbate 80, 5 to 6.5% by weight of danazol were released.

Comparative Example II

Danazol-Calcium Carbonate Composite Produced by Precipitation in a Mixing Chamber in Accordance with WO 2012/027378

Release test: after 120 min in release medium A comprising 0.1% by weight polysorbate 80, 8% by weight of the danazol were released.

According to XRD, the products had considerable fractions of crystalline calcium carbonate.

FIG. 1 shows the plasma level of the composite materials according to Examples 1, 2 and Comparative Example I.

The Plasma Levels Were Determined as Follows:

Each of 5 dogs (average weight 16 kg) was given the test substances in the same order with a break of 14 days after each application. The formulations were administered as a physical mixture of 70% test substance, 15% Avicel PH 101 (FMC BioPolymer) and 15% Kollidon CL (BASF SE) in hard gelatin capsules (Torpac Inc., USA #11). The dose was 30 mg/kg and was based individually for each animal and each application time on the actual body weight. The dogs were given the capsules on an empty stomach. Blood was taken at 3, 60, 90 min and 2, 4, 8 and 24 hours after application. Water was available ad libitum, and feeding was 4 hours after application. The plasma samples were frozen and later analyzed ((ESI(+)-LC-MS/MS) (column: Ascentis Express C18/2.7 μm/100 mm×2.1 mm/Supelco) mobile phase: acetonitrile/water (50:50 v/v) with 0.01% formic acid; detection limit (limit of quantification (LoQ)): 2-5 ng/ml)

The plasma concentration of the active ingredient is given in the FIGURE in ng/ml.

What is claimed is:

1. A process for producing composite materials by reactive spray-drying, where a liquid phase A, which comprises inorganic cations, and a liquid phase B, which comprises anions which, with the inorganic cations, form a salt that is insoluble in the mixture of the liquid phases are sprayed together using at least one multi-substance nozzle, and where at least one hydrophobic active ingredient is present in dissolved form in at least one liquid spraying phase, and where the salt formed from the cations of phase A and the anions of phase B has a solubility of less than 0.02 mol/l in the neutral aqueous medium.

2. The process according to claim 1, wherein the inorganic cations of phase A are selected from the group consisting of magnesium ions, calcium ions and zinc ions.

3. The process according to claim 2, wherein the inorganic cations of phase A used are calcium ions.

4. The process according to claim 1, wherein the liquid phase A is a solution of salts of the inorganic cations and the salts are selected from the group consisting of calcium chloride, calcium nitrate, calcium acetate, magnesium chloride, magnesium nitrate, magnesium acetate, magnesium citrate, magnesium lactate, zinc chloride, zinc nitrate and zinc acetate.

5. The process according to claim 1, wherein the liquid phase B used is a solution of salts selected from the group consisting of ammonium, alkali metal or magnesium salts of carbonates, hydrogencarbonates, sulfates, phosphates and hydrogenphosphates.

6. The process according to claim 1, wherein the liquid phase B used is a solution of salts selected from the group consisting of ammonium, alkali metal or magnesium salts of citric acid, lactic acid and oxalic acid.

7. The process according to claim 1, wherein the salt formed from the cations of phase A and the anions of phase B that is used is a calcium salt selected from the group consisting of carbonates, phosphates, sulfates, hydroxylapatites, citrates, lactates and oxalates.

8. The process according to claim 1, wherein the liquid phases are solutions and the solvents present are water or organic solvents or mixtures thereof.

9. The process according to claim 8, wherein the organic solvent used is ethanol.

10. The process according to claim 1, wherein the hydrophobic active ingredient is used in the form of an ethanolic or aqueous-ethanolic solution.

11. The process according to claim 1, wherein a surfactant is added to the liquid phase which comprises the hydrophobic active ingredient.

12. The process according to claim 11, wherein a surfactant is added in amounts of from 2 to 50% by weight, based on the amount of active ingredient, to the liquid phase which comprises the hydrophobic active ingredient.

13. The process according to claim 1, wherein a surfactant is added in amounts of from 2 to 50% by weight, based on the amount of active ingredient, to the liquid phase which comprises the hydrophobic active ingredient.

14. The process according to claim 1, wherein a surfactant selected from the group consisting of polyoxyalkylated fatty acid esters and polyoxyalkylated fatty alcohol ethers is added to the liquid phase which comprises the hydrophobic active ingredient.

15. The process according to claim 1, wherein the multi-substance nozzle used is an ultrasonic nozzle.

16. The process according to claim 1, wherein an atomization gas is used during the spray-drying.

17. The process according to claim 1, where the by spraying drops with a median diameter of 10 to 200 μm μm are produced.

18. The process according to claim 1, wherein the hydrophobic active ingredient is present in phase A.

19. The process according to claim 1, wherein the hydrophobic active ingredient is present in phase B.

20. The process according to claim 1, wherein phase A comprises a calcium salt and phase B comprises ammonium carbonate or sodium carbonate.

21. The process according to claim 1, wherein phase A comprises a calcium salt and phase B comprises ammonium acetate or sodium acetate.

* * * * *